United States Patent [19]

Stubbs

[11] Patent Number: 4,624,258

[45] Date of Patent: Nov. 25, 1986

[54] CERVICAL DILATOR WITH CAPTIVE EXTRACTION ELEMENT

[75] Inventor: George Stubbs, Los Angeles, Calif.

[73] Assignee: Milex Products, Incorporated, Chicago, Ill.

[21] Appl. No.: 649,504

[22] Filed: Sep. 11, 1984

[51] Int. Cl.⁴ ............................................. A61M 29/02
[52] U.S. Cl. ...................................... 128/341; 128/130
[58] Field of Search ............... 128/341, 343, 344, 130; 524/916; 523/121; 604/904, 368

[56] References Cited

U.S. PATENT DOCUMENTS 4,237,893 12/1980 Michaels ............................. 128/341
4,467,806 8/1984 Bhiwandiwala et al. ........... 128/341
4,480,642 11/1984 Stoy et al. ........................... 128/341

Primary Examiner—Gene Mancene
Assistant Examiner—John G. Weiss
Attorney, Agent, or Firm—Russell E. Hattis; Stephen R. Arnold

[57] ABSTRACT

A cervical dilator assembly features a captive extraction element in the form of a collar press-fitted over one end of an insertion element made of the self-swelling vegetable stalk *laminaria japonica*. A withdrawal cord is affixed to the collar, the collar being captively retained in the swollen condition of the inserted dilator element so that pull on the cord causes withdrawal of the inserted dilator element without rupture or tearing thereof. In the preferred form of the invention the collar is fabricated in the form of a migration-limiting disc.

12 Claims, 6 Drawing Figures

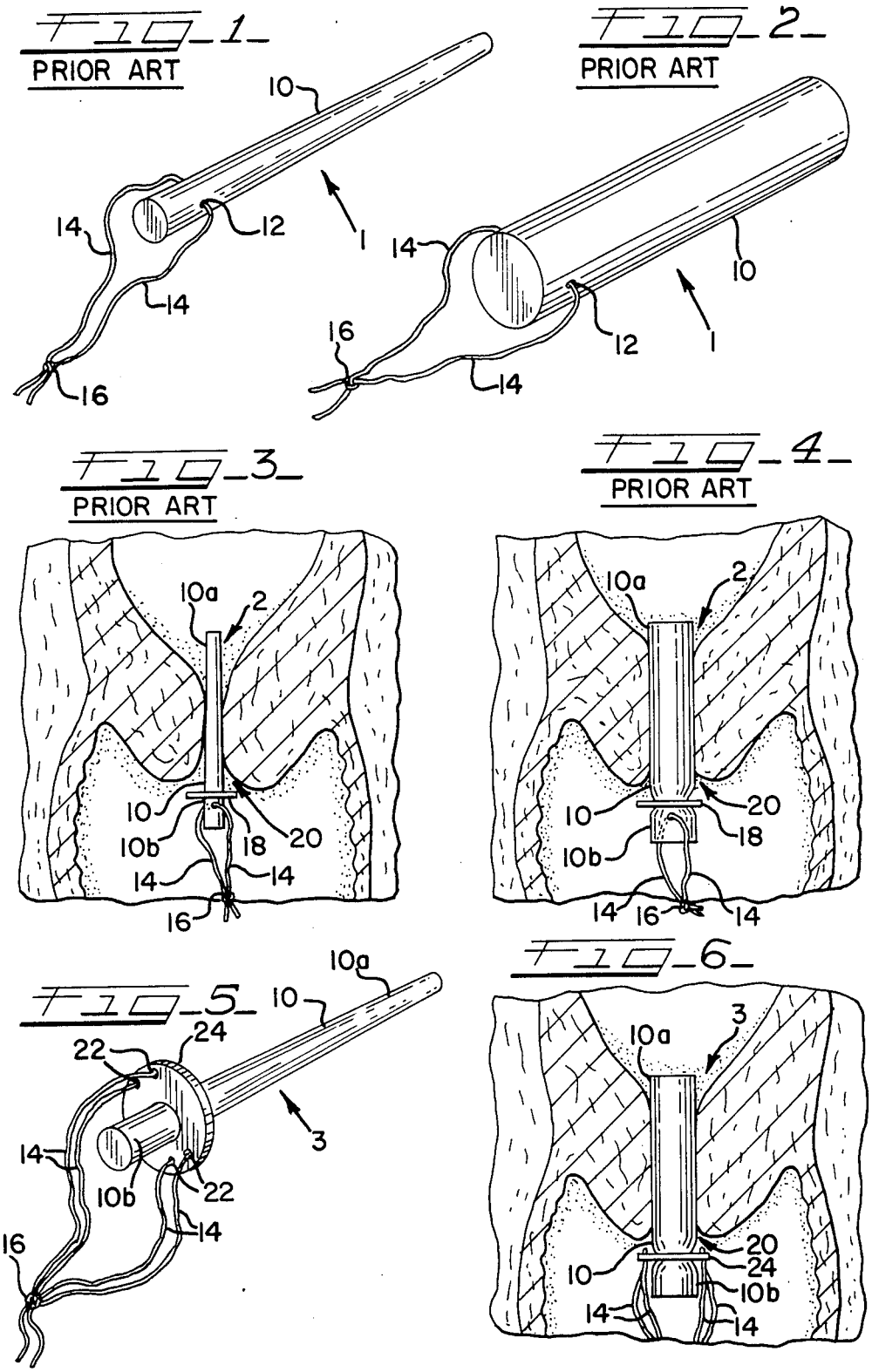

CERVICAL DILATOR WITH CAPTIVE EXTRACTION ELEMENT

TECHNICAL FIELD OF THE INVENTION

The technical field of the invention is manually operable medical instruments, in particular those instruments normally used for cervical dilation.

BACKGROUND OF THE INVENTION

In the treatment of female patients, a physician on occasion finds it necessary to dilate and/or soften the cervix of the patient. Such dilation is frequently a prerequisite for placement and removal of intrauterine devices, induction of labor, radium placement, drainage of the uterine cavity, endometrial biopsy procedures, uterine curettage, and for a variety of other reasons. A variety of insertion elements used for dilation purposes are known to the art, and well-known among these is a cervical dilator employing a central longitudinally tapered rod-like insertion element made from the root stalk of a seaweed known as *laminaria japonica*, such insertion elements having been used for over one hundred years for insertion into the cervix to expand the cervical canal. The prior art has long recognized the unique property of this material, namely that when inserted in the dry state into the cervical canal a rod of given diameter will, upon absorption of fluids normally present in the cervical canal expand principally in the radial direction by a factor of 200 to 300 percent. This action slowly and automatically expands the canal over a period of several hours. These elements are normally both inserted and removed by a physician.

A rigid disc-like collar member is generally placed around the rod-like dilator element to act as a stop shoulder to limit the degree of extension of the dilator element into the cervical canal. This prevents premature migration of an inserted dilator element undesirably high in the cervical canal before the requisite anchoring expansion takes place. The stop collar member has a central aperture which receives the dilator element which projects both forwardly and rearwardly therefrom. The collar member has a diameter much larger than the diameter of the entrance of the cervical canal. The collar member initially is held upon the dilator element only by friction between the dilator element press-fitted into the collar member and the defining wall of the collar aperture.

Usually a thread loop is affixed to the rear of the dilator element through a small passage drilled therethrough, the thread serving as a tell-tale to assist the physician in locating the end of the dilator element for withdrawal thereof. The structural strength of the stalk is inadequate, particularly in the wet and expanded form, to support sufficient force to allow the cord to be used reliably for extraction purposes; hence the physician normally uses the cord only as a "tell-tale" to aid in locating the dilator element so that it can be withdrawn by application of forceps. Sometimes if the physician uses the cord to pull the dilator element from the cervical canal, the cord tears through the element before it is completely removed from the canal.

It would be a useful feature to be able to reliably secure such a cord to the dilator element in such a way that the element may be withdrawn by a pulling force on the cord without tearing it loose therefrom. While it would seem possible to securely anchor the cord by using suitable adhesives for this purpose, to the applicant's knowledge this has not heretofore been done, probably because chemical adhesives can possibly be torn or act as an irritant within the cervical canal.

SUMMARY OF THE INVENTION

It has not been heretofore appreciated that the collar member could act as a secure anchoring point for the tell-tale cord, so that the cord if attached thereto could be grasped and pulled to remove the fluid-expanded dilator element from the cervical canal making a forceps removal thereof unnecessary. However, the applicant has found that the portion of the dilator element projecting behind the stop collar member becomes wetted by the fluids of the cervix and cervical canal by capillary action and expands to about the same degree as the portion thereof without the canal, and that the dilator can act as a reliable anchoring point for the "tell-tale" cord. Thus, according to a feature of the invention, the stop collar member is provided with apertures in which the "tell-tale" cord is anchored so that the cord can be grasped and pulled to withdraw the dilator element from the cervical canal without tearing the cord loose therefrom.

Other features and advantages of the invention will become apparent upon making reference to the description to follow, the drawings, and the claims.

DESCRIPTION OF DRAWINGS

FIG. 1 is a perspective view of a simple prior art cervical dilator element fabricated from a stalk of *laminaria japonica* and having a "tell-tale" cord fastened therethrough via a transverse hole proximate to one end of the element.

FIG. 2 shows the dilator element in the expanded condition after exposure to cervical fluid.

FIG. 3 shows a somewhat improved prior art version of the cervical dilator element of FIG. 1 inserted into the cervical canal, the improved dilator element having a stop collar member attached thereto to prevent undesirable inward migration of the dilator element into the cervical canal before anchoring expansion thereof.

FIG. 4 shows the dilator element assembly of FIG. 3 in the expanded form.

FIG. 5 shows the dilator element assembly of the present invention showing the migration-limiting collar attached proximate to the outer end thereof, and having the withdrawal cord fastened to the stop collar member instead of the insertion element.

FIG. 6 shows the assembly of FIG. 5 inserted and in the expanded form.

DETAILED DESCRIPTION OF THE PREFERRED FORM OF THE INVENTION

The present invention discloses an assembly whereby a strongly attached extraction and "tell-tale" cord may be affixed to a fragile self-expanding cervical dilator element. FIGS. 1 and 2 show a simple form of prior art cervical dilator assembly 1 made from a stalk of the vegetable material *laminaria japonica*, FIG. 1 showing a rod-shaped dilating element 10 of this material and having a cord loop 14 attached thereto via a transverse hole 12 proximate to one end thereof, the cord loop being captively secured in by an end knot 16. FIG. 2 shows the same assembly 1 after immersion in fluids normally present in the cervix, the dilating element 10 now being substantially expanded, principally in a radial direction as a result of internal swelling which is characteristic of this particular vegetable stalk.

FIG. 3 shows an improved prior art form of such a dilator assembly 2 inserted into the cervical canal 20, the assembly having press-fitted thereto a disc-shaped stop collar member 18 proximate to the cord-carrying end 10b. The dilator assembly is here shown immediately after insertion with the dilating element 10 in the unexpanded condition, the interior end 10a thereof exiting the interior end of the cervical canal 20. The purpose of the stop collar member 18 is to prevent excessive inward migration of the dilating element 10 into the cervical canal 20 before sufficient swelling has taken place to anchor it into position.

FIG. 4 shows the same assembly 2 in the expanded form.

Because the dilating element 10 is fabricated from a longitudinal section of the seaweed stalk *laminaria japonica*, the capillaries of the stalk are thus oriented axially, with the result that during exposure to cervical fluids at the interior end 10a (FIG. 3), these fluids migrate lengthwise through the element and cause the exterior 10b to similarly swell.

The present invention is based upon the recognition that this radial swelling rigidly secures the stop collar member 18 to the dilator element 10 without the use of toxic or irritating adhesives, and further that an extracting force, if applied to the collar member instead, will be uniformly transmitted to the dilator element to avoid tearing the element, as is readily possible if the pulling force on a cord is concentrated at the attaching point to the dilator element. The invention takes the form of the assembly 3 shown in FIG. 5. A circular disc-shaped stop collar member 24 preferably dimensional similarly to that of the stop collar member 18 of FIGS. 3 and 4 is similarly press-fitted over one end 10b of the dilating element 10, the collar member being configured with two pairs of holes 22 centered on a common line passing through the center of the collar member through which a pair of cords 14 are respectively looped and secured as shown. The ends of the cords are grouped together and secured by means of a knot 16.

FIG. 6 shows the assembly 3 inserted into the cervical canal 20 and in the swollen state thereof. Here, it will be noted that the cord loops 14, being secured to the disc 24, cannot exert a local lengthwise tearing force on the dilating element 10 as shown in FIGS. 1-4, but rather pull directly on the collar 24, now captively secured by the previously mentioned swelling action of the dilating element. The assembly 3 may then be withdrawn by a simple pull on the cords 14 to remove the assembly 3 from the patient, without necessitating the customary use of forceps to grasp the outer end 10b of the dilator element 10.

While in the preferred form of the invention the collar member 18 performs the double function of dilator element insertion-limiting as well as extraction, the broadest aspect of the invention is the use of separate collars for these purposes.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore it is intended that the invention not be limited to a particular embodiment disclosed as the best mode contemplated for carrying out the invention, but that the broadest aspects of the invention will include all embodiments and equivalents falling within the scope of the general principles disclosed herein. Thus, the principles of the present invention may be applied to expandable similarly fragile cervical dilator elements other than those made of *laminaria japonica*.

I claim:

1. A cervical dilator assembly comprising:

a generally longitudinally tapered rod-shaped dilating element configured for insertion into the cervical canal, said element having the property of undergoing substantial radial expansion when in contact with fluids normally present in or adjacent said canal;

substantially non-expandable collar means having an aperture through which said dilating element extends wherein said collar means is captively secured around a portion of said dilating element in the unexpanded state of said rod-shaped element with portions of said element axially extending forwardly and rearwardly past both sides of said collar means, the expansion of said dilating element forwardly and rearwardly of said collar means resulting from said contact with said fluids securely anchoring said collar means thereto; and hand grippable means affixed to said collar means for allowing a pulling force to be applied directly to said collar means so as to withdraw said dilating element from the cervical canal when said element is in said expanded state on both sides of said collar means.

2. The dilator assembly of claim 1 wherein said collar means is disc-shaped and adequately large in diameter to substantially impede migration of the outer end of said dilating element into said canal when the inner end of said dilating element is so inserted therein, said dilating element by capillary action drawing fluids along its entire length so that even the portion thereof outside said cervical canal expands as a result thereof.

3. The dilator assembly of claim 1 wherein said collar has hole means therein, and said hand grippable means comprises cord means threadingly affixed to said collar means through said hole means.

4. The dilator assembly of claim 3 wherein said hole means comprises two pairs of holes centered along a common diameter and said cord means comprises separate cords looped respectively through said pairs of holes and tied together at their ends.

5. The dilator assembly of claim 1 wherein said dilating element is made of the vegetable stalk *laminaria japonica*.

6. The dilator assembly of claim 1 wherein said collar means is captively secured to said dilating element in the unexpanded state by press-fitting said collar means over said dilating element.

7. The dilator assembly of claim 1 wherein said collar means is configured as a circular disc-shaped element, said aperture has a cross-sectional configuration corresponding substantially to the cross-sectional configuration of said dilating element in its unexpanded state so as to be slidable over said dilating element where it is retained thereon by the friction therebetween.

8. The dilator assembly of claim 2 wherein said collar means has hole means therein, and said hand grippable means includes cord means threadingly affixed to said collar means through said hole means.

9. The dilator assembly of claim 2 wherein said dilating element is made of the vegetable stalk *laminaria japonica*.

10. The dilator assembly of claim 2 wherein said collar means is captively secured to said dilating element in the unexpanded state by press-fitting said collar means over said dilating element.

11. The dilator assembly of claim 2 wherein said collar means is configured as a generally circular disc, and said aperture has a cross-sectional configuration corresponding substantially to the cross-sectional configuration of said dilating element in an unexpanded state so as to be slidable over said dilating element and retained thereon by a friction therebetween.

12. A cervical dilator assembly comprising:
   a generally longitudinally tapered rod-shaped expandable dilating element of *laminaria japonica* configured for insertion into the cervical canal;
   a substantially non-expandable generally circular one-piece disc-shaped collar element having a generally circular central opening passing through the center thereof and press-fitted over said dilating element in the unexpanded state thereof to be captively secured therearound near but spaced from the outer end thereof, said collar element being of adequate diameter to substantially impede migration of said outer end of said dilating element into said canal when the inner end of said dilating element is inserted thereinto; and
   cord means affixed to said collar element for allowing a pulling force to be applied to said collar element so as to withdraw said dilating element from the cervical canal when said element is in an expanded captive state on both sides of said collar element as a result of contact with fluids normally in or adjacent said canal, said collar element having at least a pair of holes on opposite sides thereof, said cord means being loopingly attached through said holes to opposite sides of said collar element so that with said dilating element in an expanded state on both sides of said collar element an outward pull on said cord means applies a local force to said collar element proximate to said holes to urge said dilating element out of said canal.

* * * * *